United States Patent [19]
Takao et al.

[11] Patent Number: 6,070,450
[45] Date of Patent: Jun. 6, 2000

[54] MULTILAYERED GAS SENSOR

[75] Inventors: Yasumasa Takao; Masanobu Awano; Mutsuo Sando, all of Aichi, Japan

[73] Assignee: Japan as represented by Director General of Agency of Industrial Science and Technology, Tokyo, Japan

[21] Appl. No.: 09/248,319

[22] Filed: Feb. 11, 1999

[30] Foreign Application Priority Data

May 20, 1998 [JP] Japan .................................. 10-156741

[51] Int. Cl.$^7$ .......................... G01N 27/12; G01N 25/00; G01N 27/00; H01C 7/00
[52] U.S. Cl. ......................... 73/31.05; 73/31.05; 73/23.2; 73/23.31; 422/90; 422/98; 204/429; 338/34
[58] Field of Search ............................... 73/31.05, 31.06, 73/23.2, 23.31, 31.01; 422/98, 88, 83, 90; 338/22 SD, 34; 204/429, 434

[56] References Cited

U.S. PATENT DOCUMENTS

| | | | |
|---|---|---|---|
| 4,584,867 | 4/1986 | Forster | 73/23 |
| 4,586,143 | 4/1986 | Kaneyasu et al. | 364/509 |
| 5,145,645 | 9/1992 | Zakin et al. | 422/98 |
| 5,217,692 | 6/1993 | Rump et al. | 422/98 |
| 5,296,196 | 3/1994 | Takeshima | 422/98 |
| 5,367,283 | 11/1994 | Lauf et al. | 338/34 |
| 5,605,612 | 2/1997 | Park | 204/429 |
| 5,698,771 | 12/1997 | Shields et al. | 73/31.05 |
| 5,866,075 | 2/1999 | Gupta et al. | 422/88 |
| 5,889,198 | 3/1999 | Reitmeier et al. | 73/25.05 |
| 5,935,398 | 9/1999 | Taniguchi et al. | 204/424 |
| 5,939,615 | 8/1999 | Kato et al. | 73/31.05 |
| 5,948,965 | 9/1999 | Upchurch et al. | 73/23.31 |

OTHER PUBLICATIONS

K. Tsuda, "The Most Recent Technological Trends in Inflammable Gas Sensors", New Ceramics & Electronic Ceramics, No. 12, 1997, pp. 27–32.

N. Miura, et al. "Surface Modification in Semiconductor Gas Sensors", Surface, vol. 28 No. 1, 1990, pp. 15–25.

H. Ohnishi, et al. "Sensing Properties of Highly Selective Methane Sensor Based on $SnO_2$ Thin Film", Japanese Ceramic Association, Autumn Symposium Summary For Lecture, 1996, p. 240.

N. Yamazoe, et al. "The Role of Metal Microparticles in Semiconductor Gas Sensors", Surface, vol. 27 No. 6, 1989, pp. 499–507.

M. Haruta, "Gold Super–Microparticle Solid Oxides as Room–Temperature Catalysts", Surface, vol. 28 No. 5, 1990, pp. 333–342.

C.D. Feng et al. "Effect of Gas Diffusion Process on Sensing Properties of $SnO_2$ Thin Film Sensors in a $SiO_2$ Layer–Built Structure Fabricated by Sol–Gel Process", J. Electochem. Soc., vol. 141 No. 1, 1994, pp. 220–225.

*Primary Examiner*—Hezron Williams
*Assistant Examiner*—J. David Wiggins
*Attorney, Agent, or Firm*—Oblon, Spivak, McClelland, Maier & Neustadt, P.C.

[57] ABSTRACT

The present invention provides a gas sensor element having physical, electrical and chemical properties capable of detecting methane and carbon monoxide selectively with 1 intergrated filtering, catalyzing sensor by improving gas selectivity of the semiconductor gas sensor. The present invention relates to a gas sensor element, which has a carbon monoxide sensor layer with an ability to function as a catalyst film that blocks carbon monoxide, which impedes detection of methane, and has a layer-built structure where the surface of a methane sensor is covered with the carbon monoxide gas sensor which can be obtained by a gas-phase method.

5 Claims, 7 Drawing Sheets

MULTILAYERED GAS SENSOR

TECHNICAL FIELD

The present invention relates to a novel semiconductor gas sensor element, and in further detail, to a semiconductor gas sensor which can detect several gases at good selectivity with 1 element and has a layer-built structure, wherein the surface of a sensor for city gas, whose main components are methane and the like, is covered with a sensor for incompletely burned gases, such as carbon monoxide and the like.

BACKGROUND ART

Gas sensors are widely used to detect leaks of inflammable gases, such as hydrogen and ethanol, etc., and have recently been used for detection of aromatic components and toxic gases in food and environment-related fields. Therefore, as gas-sensing properties of gas sensors, elavation of detectability of smaller amounts of minor components from the gases in question, improvement of gas selectivity, expansion of the types of gases to be detected and the like are requested.

Moreover, in the inflammable gas sensors used for city gas alarm devices and the like, which hold a big share of the gas sensors, there is a need for sensors capable of detecting city gas, such as methane gas and the like, and simultaneously of detecting incompletely burned gas for preventing carbon monoxide poisoning and the like. As the hybrid-type gas leak alarms for city gas and incompletely burned gases developed thus far, multidevice-type alarms with a sensor for methane gas and a sensor for carbon monoxide are generally used and each of these sensors are controlled with a computer, and therefore, there is a limit to the extent of the alarms to be miniaturized. A so-called 1-element type sensor capable of differentiating and detecting city gas and incompletely burned gases with 1 sensor by changing operating conditions, including operating temperature and the like of the sensor, has not been marketed yet and therefore, there is still room for improvement [for instance, K. Tsuda, "The Most Recent Technological Trends in Inflammable Gas Sensors", Nyu Seramikkusu (New ceramics), No. 12, p27–32, (1997)].

Methane gas, which accounts for approximately 90% of city gas, is one of the inflammable gases with low chemical activity and it is difficult to detect only methane with a semiconductor gas sensor. As a countermeasure to the above-mentioned problem, by using a method of adding a sensitizer (catalyst) such as Pd or the like, or a method of using needle-shaped semiconductor particles with large surface area which can increase reaction space and improve gas diffusivity, selectivity of the gas sensor to methane, which is relatively non-inflammable, can be improved, and, for example, gas sensitivity (temperature of 300 to 500° C.) of 10 to 20 to 0.5% methane is obtained [for instance, N. Miura et al., "Surface Modification in Semiconductor Gas Sensors", Hyomen (Surface), vol. 28, No. 1, p15–25, (1990), H. Ohnishi et al., "Sensing properties of highly selective methane sensor based on $SnO_2$ thin film", Nihon Seramikkusu Kyokai Shuki Shinpojiumu Koen Yokoshu (Japanese Ceramic Association, Autumn Symposium Summary for Lecture), p240, (1996)]. Besides, the sensitivity is defined as a ratio of the electrical resistance of a sensor in air (Ra) to that in a sample gas (Rg).

With respect to gas sensors for incompletely burned gases, such as carbon monoxide and the like, which require detectability of even smaller amounts of minor components of the gases for preventing poisoning compared with that for city gases, and it is reported that the temperature at which maximum sensitivity is obtained shifts to the low-temperature side and sensitivity of the sensors is improved by adding Pd and Au due to the effects of these sensitizers. For instance, gas sensitivity (Ra/Rg) of 10 to 20 to 0.02% carbon monoxide is obtained when Pd is added [for instance, N. Yamazoe et al., "The Role of Metal Microparticles in Semiconductor Gas Sensors", Hyomen (Surface), vol. 27, No. 6, p499–507, (1989); M. Haruta, "Gold Super-Microparticle Solic Oxides as Room-temperature Catalysts", Hyomen (Surface), vol. 28, No. 5, p333–342, (1990)].

Methods have been studied whereby a layer-built structure having the sensor layer surface covered with a catalyst layer or filter layer is used in order to expend or block components other than the desired gases as a purpose for improving selectivity of specific gases in a mixture of several gases. However, problems with gas diffusivity have been pointed out in this method and further it is reported that it takes longer periods until electrical symbols stabilize compared with the case where a coating layer is not used [for instance, C. D. Feng et al., "Effect of Gas Diffusion Process on Sensing Properties of $SnO_2$ Thin Film Sensors in a $SiO_2/SnO_2$ Layer-Built Structure Fabricated by Sol-Gel Process," J. Electrochem. Soc., Vol. 141, p220–225 (1994)]. Moreover, the fuction of the coating layers have been tested hitherto as catalysts or filters, etc., and coating layers have not been used as separate gas sensors.

In order to solve the disadvantages of the above-mentioned type of conventional semiconductor gas sensors, the present invention has been developed and this invention provides a semiconductor gas sensor element which is useful for obtaining a sensor capable of detecting several gases with good selectivity by 1 element and has a layer-built structure where the surface of a methane sensor is covered with a carbon monoxide sensor.

The inventors have performed intense research to develop a 1 element type semiconductor gas sensor capable of detecting methane and carbon monoxide with good selectivity and as a result, they have focused on the fact that since methane has a low chemical activity, somewhat high temperature is needed to detect the gas, and conversely, it is possible to shift sensitivity to carbon monoxide higher on the low-temperature side and lower at a high temperature by using a sensitizer. They also have studied application of a coating technology in order to control the morphology of the semiconductor particles of the methane sensor in view of detecting methane gas with low activity and further detecting several gases. That is, the inventors have made a layer-built structure where a carbon monoxide gas sensor is coated on the surface of a methane gas sensor to give the carbon gas sensor layer the ability to function as a catalyst film that blocks carbon monoxide, which prevents the detection of methane. They have discovered that their purpose can be accomplished based on the improvement in gas diffusivity that is obtained by using a porous layer-built structure whose sensor layers are formed with rosary beads and the like. They have successfully completed the present invention based on these knowledge.

SUMMARY OF INVENTION

The present invention relates to improving gas selectivity of the semiconductor gas sensor and provides a gas sensor element capable of detecting methane and carbon monoxide selectively with 1 sensor.

The present invention relates to a gas sensor element, characterized by having a carbon monoxide sensor layer which has an ability to function as a catalyst film that blocks carbon monoxide, which impedes detection of methane, and by using a layer-built structure where the surface of a methane sensor is covered with a carbon monoxide gas sensor obtained by the gas-phase method.

By means of the present invention, it is possible to provide a sensor element capable of detecting several gases with good selectivity by 1 element, which is useful for a gas sensor.

DISCLOSURE OF THE INVENTION

That is, the present invention provides a semiconductor gas sensor, characterized in that it can detect methane and carbon monoxide with good selectivity with 1 sensor and has a layer-built structure where the surface of a methane sensor is covered with a carbon monoxide sensor.

In order to solve the above-mentioned subjects, the following constituents are adopted by the present invention:

(1) A semiconductor gas sensor element, comprising a layer-built structure of a methane sensor and a carbon monoxide sensor, wherein the surface of the methane sensor is covered with the carbon monoxide sensor, and the carbon monoxide sensor layer has an ability to act as a catalyst film capable of blocking the carbon monoxide, which impedes detection of methane, and having physical, electrical and chemical properties capable of detecting both methane and carbon monoxide with good selectivity by 1 sensor element.

(2) The semiconductor gas sensor element according to (1), wherein said methane sensor is made from a needle-shaped semiconductor particles as starting materials, and has a increased high reactivity to methane at a high temperature and simultaneously a low reactivity to methane at a low temperature.

(3) The semiconductor gas sensor element according to (1), wherein said carbon monoxide is made from semiconductor-metal composite particles which are obtained by depositing metal particles with catalyst function on the surface of semiconductor gas sensor material particles synthesized by the gas phase method as the starting material, and has a increased high sensitivity to carbon monoxide on the low-temperature side and decreased low sensitivity at a high temperature.

(4) The semiconductor gas sensor element according to (1), wherein needle-shaped semiconductor particles and semiconductor-metal composite particles are used as the starting material, and a porous thick film structure where these starting materials are deposited on a substrate in the form of rosary beads by electrostatic deposition.

(5) The semiconductor gas sensor element according to (1), wherein the methane sensor is an $SnO_2$ based one and the carbon monoxide sensor is an $SnO_2$—Pd based one.

The present invention will now be explained in further detail.

In the present invention, firstly, semiconductor gas sensor material particles for the methane sensor are synthesized. With respect to these semiconductor gas sensor material particles, it is preferable to control their forms so as to detect methane with low activity. Needle-shaped $SnO_2$ particles synthesized by evaporation-condensation methods are given as an example, but there are no special restrictions to the semiconductor particles.

Next, the semiconductor gas sensor material particles are charged with positive or negative static electricity, and then a sensor substrate to which internal electrodes have been pre-attached is charged or grounded with the opposite polarity to that of the semiconductor particles to deposite the semiconductor particles electrostatically on the substrate. At this time, the semiconductor particles are deposited or intertwined with one another in the form of rosary bead due to a power capable of forming rosary bead that is caused when the charged particles are being deposited on the substrate and a sensor element with the particles deposited at high porosity obtained. The bi-directional impact charging method is exemplified as an example, but there are no special restrictions to the method of charging the particles at this time.

Once the methane sensor layer is prepared, carbon monoxide gas layer is laminated on the surface of the methane sensor layer. The semiconductor gas sensor material particles and catalyst particles and the like are synthesized by the CVD method and the like as the starting materials for the carbon monoxide sensor. In this method, semiconductor particles, such as $SnO_2$, etc., are exemplified as an example for the gas sensor material particles, and metal particles, such as Pd, etc., are given as examples of the catalyst particles, but there are no special restrictions to these gas sensor material particles or catalyst particles in this case.

Next, an electro static charge of any volume and polarity is applied to the gas sensor material particles and the catalyst particles and then both are mixed. As a result, composite particles where catalyst particles have been deposited on the surface of the gas sensor material particles are synthesized under the power of the electrostatic cohesion that is caused between the particles being charged to opposite polarities. The bi-directional impact charging method is given as an example, but there are no particular restrictions to the method of charging the particles at this time.

Once thus obtained composite particles of gas sensor material particles and catalyst particles are charged with positive or negative static electricity, the sensor substrate with the methane sensor layer is charged or grounded with the opposite polarity of the composite particles to deposite the composite particles electrostatically on the methane sensor surface. Internal electrodes for carbon monoxide are pre-attached to the substrate in this case. A multilayer sensor with a layer-built structure where the surface of the methane sensor is covered with a carbon monoxide sensor is made as previously described.

Figure 1:
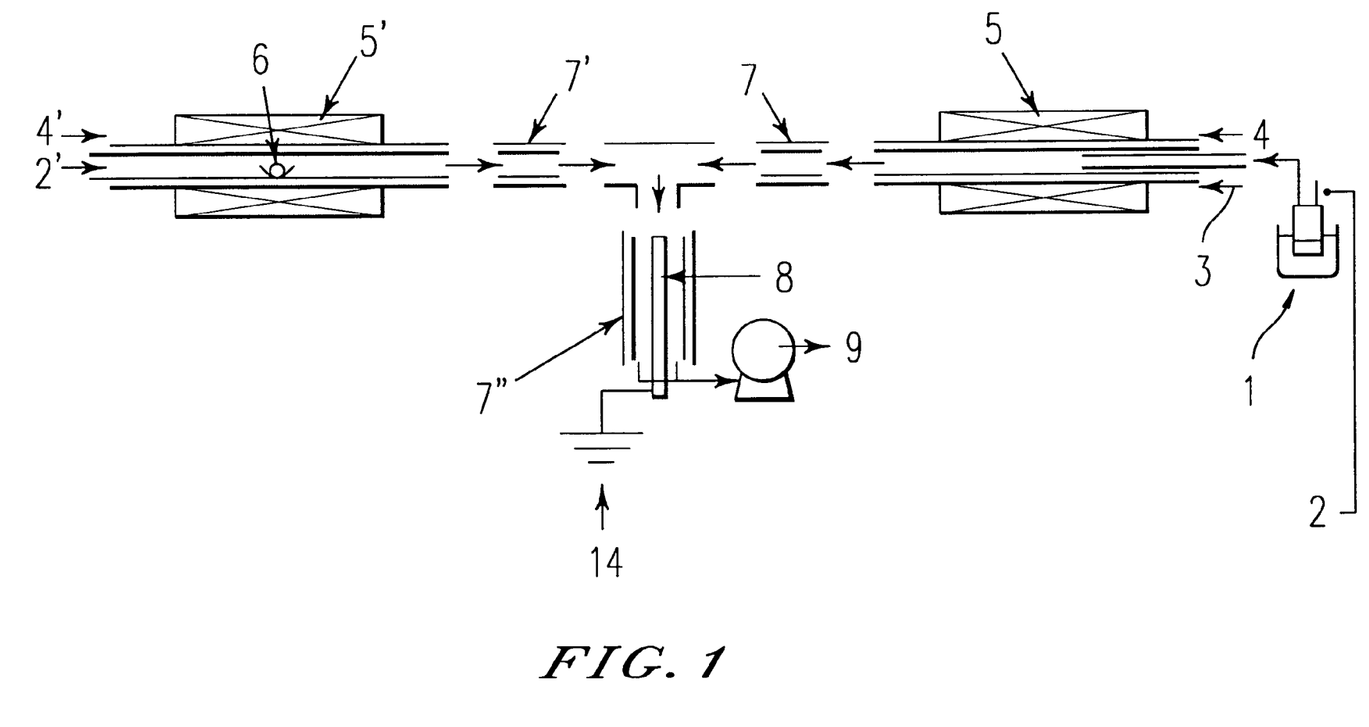
FIG. 1 is an explanatory drawing of 1 example of the apparatus for executing the present invention.
Figure 2:
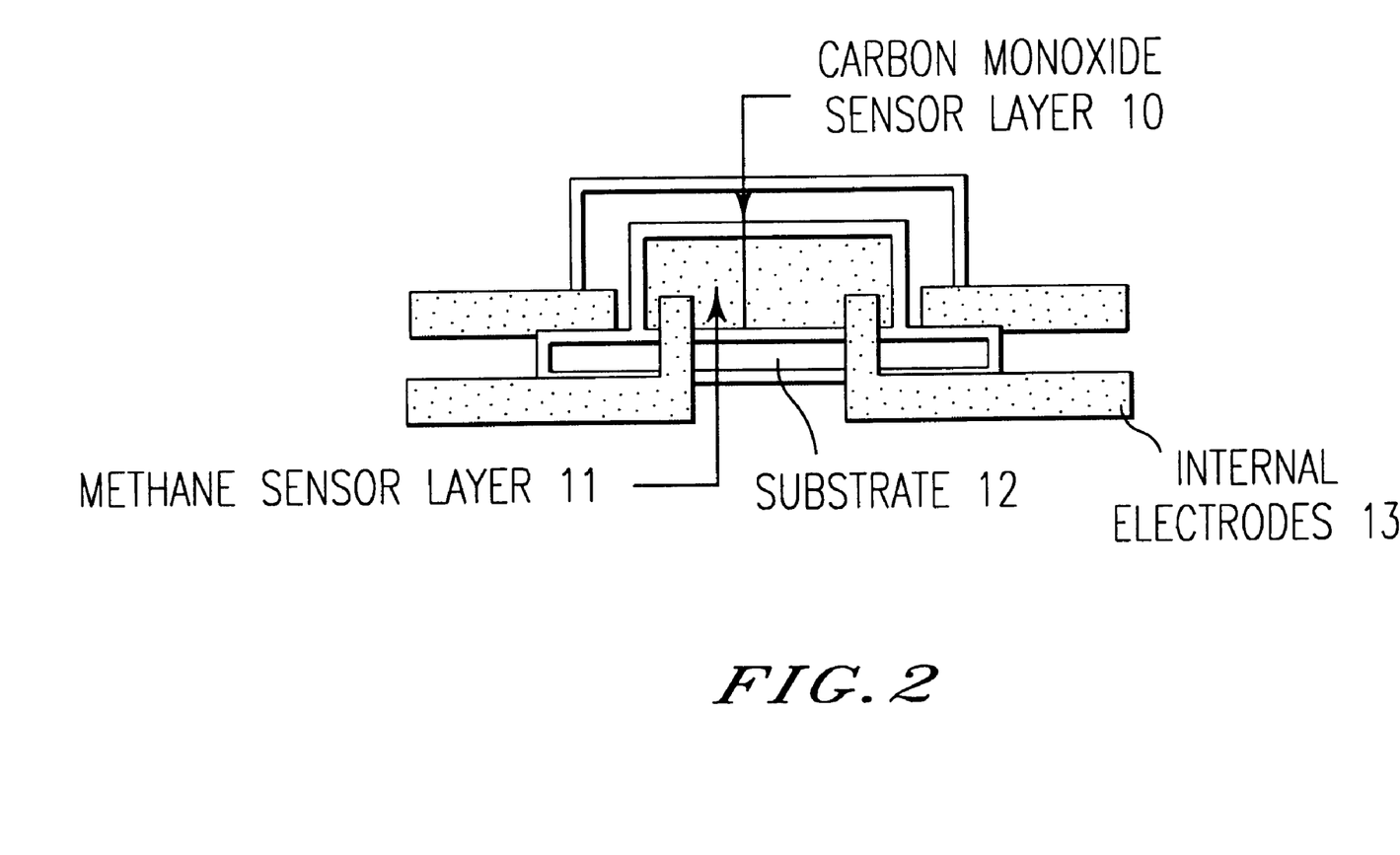
FIG. 2 is an explanatory drawing of 1 example of the gas sensor obtained by the present invention.

The present invention will now be described using the attached drawings. FIG. 1 is 1 example of the apparatus for fabricating a layer-built sensor with a layer-built structure where the surface of a methane sensor is covered with a carbon monoxide sensor of the present invention, and FIG. 2 is a schematic diagram of 1 example of the layer-built gas sensor obtained using the apparatus in FIG. 1.

By means of the method in FIG. 1, firstly, Sn starting powder 6 is placed in reaction vessel 5' as the semiconductor particles for the methane sensor and reaction vessel 5' is heated to 1,500 to 1,700° C. to generate vapor thereof. $N_2$ is fed as carrier gas 2' at 1 to 5 liters/minutes, while $N_2$ (for instance, 5 liters/minutes) is fed as sheath gas 4' to synthesize $SnO_2$ gas sensor material particles having needle-shaped forms controlled by an evaporation-condensation reaction in reaction vessel 5'.

Then thus obtained $SnO_2$ needle-shaped particles are transferred to charging vessel 7" and are charged with, for instance, negative static electricity. Then sensor substrate 8, to which internal electrodes have been pre-attached, is, for instance, grounded to deposit the needle-shaped particles electrostatically on the substrate. As a result, an $SnO_2$ gas sensor is obtained where needle-shaped particles are intertwined with one another and are deposited in a porous state of high porosity due to a power capable of forming rosary beads that is caused when the charged particles are deposited on the substrate. The gas that has transferred the particles, etc., is evacuated with pump 9.

It is revealed that by means of the above-mentioned method, needle-shaped particles for the $SnO_2$ gas sensor with a length of, for instance, several 100 nm or longer are obtained. Moreover, it is also revealed that a porous thick film structure can be made where the above-mentioned needle-shaped particles are deposited in a state where the particles are intertwined with one another by an electrostatic deposition. This thick film structure was retained, even after annealing thereof. It is further revealed that the above-mentioned semiconductor needle-shaped particles of the thick film structure are excellent as a sensor of inflammable gases.

Next, tetramethyl tin $Sn(CH_3)_4$ is brought to its gasification temperature of 0° C. in vapor generator 1 to generate $Sn(CH_3)_4$ vapor. The obtained $Sn(CH_3)_4$ vapor is transferred to reaction vessel 5, which is kept at a temperature of 500 to 800° C., using Ar at 0.01 to 0.5 liters/minute as carrier gas 2, while $O_2$ at 0.1 to 0.5 liters/minutes as reaction gas 3 and $N_2$ at 0 to 5 liters/minute as sheath gas 4 are simultaneously fed to synthesize the $SnO_2$ gas sensor material particles as the semiconductor particles for the carbon monoxide sensor by a chemical reaction inside reaction vessel 5.

Pd starting powder 6 is placed in reaction vessel 5' (in this case, the above-mentioned Sn starting powder has been removed from reaction vessel 5'), and reaction vessel 5' is heated to 1,500 to 1,700° C. to generate vapor thereof. $N_2$ at 1 to 5 liters/minute is fed as carrier gas 2' and $N_2$ (for instance, 5 liters/minutes) is fed as sheath gas 4' and the Pd catalyst particles are synthesized by an evaporation-condensation reaction inside reaction vessel 5'.

Next, in order to prevent deposition on the wall surface of the vessel due to thermal diffusion, $N_2$ that had been pre-heated in a furnace is fed in sheath form and the $SnO_2$ gas sensor material particles obtained are transferred to charging vessel 7, while Pd catalyst particles are transferred to charging vessel 7' and an electrostatic charge of any volume and polarity (for instance, positive charge to the $SnO_2$ and negative charge to the Pd, etc.) is applied. Then the two are mixed to synthesize composite particles where Pd catalyst particles are deposited on the surface of $SnO_2$ gas sensor material particles by a power of the electrostatic cohesion that works between the particles charged to opposite polarities.

Next, for instance, negative electrostatic charge is applied to the $SnO_2$—Pd composite particles and then the sensor substrate for the methane sensor (in this case, it is needed to remove the $SnO_2$ needle-shaped particles deposited on the above-mentioned internal electrodes for the carbon monoxide sensor) is, for instance, grounded to deposite the composite particles electrostatically on the substrate. As shown in FIG. 2, a layer-built sensor is obtained on which composite particles are deposited in a porous state of high porosity under a power capable of forming rosary bead that is caused when the charged particles are deposited on the substrate. The gas used to transfer the particles, etc., is evacuated by pump 9.

It is revealed that by means of the above-mentioned method, composite particles where Pd particles on a nanometer order are uniformly deposited on the surface of $SnO_2$ nucleus particles with a length of, for instance, 50 to 100 nm are obtained. Moreover, as a result of measuring the electrification quantity of the particles with a Faraday gauge ammeter, it is revealed that the particles are charged up to the saturated electrification quantity of single polarity by the charging vessel. On the other hand, it is revealed that when $SnO_2$ particles and Pd particles are mixed without charging, there is a region where the two are separately trapped and do not form composite particles, and the above-mentioned method in the present invention is therefore the first to give composite particles. Moreover, it is also clarified that the above-mentioned composite particles having a porous, thick film structure where particles are laminated in the form of rosary beads are obtained by electrostatic deposition. This thick film structure of the composite particles are retained, even after annealing thereof. It is revealed that semiconductor-metal composite particles with the above-mentioned thick film structure have an excellent sensor function for inflammable gases.

SYMBOLS

1 Vapor generator
2 Carrier gas
2' Carrier gas
3 Reaction gas
4 Sheath gas
5 Reaction vessel
5' Reaction vessel
6 Starting powder
7 Charging vessel
7' Charging vessel
7" Charging vessel
8 Sensor substrate
9 Pump
10 Carbon monoxide sensor layer
11 Methane sensor layer
12 Substrate
13 Internal electrodes
14 Ground

BEST MODE FOR CARRYING OUT THE INVENTION

The present invention will now be explained in further detail with examples, but the present invention in no way limited to these examples.

The $SnO_2$ semiconductor gas sensor elements in present examples were made by the apparatus and hod demonstrated in FIG. 1.

EXAMPLE 1

(1) Method $SnO_2$ needle-shaped particles were synthesized by the evaporation-condensation method in a reducing gas.

Sn starting powder 6 was introduced to reaction vessel 5' and reaction vessel 5' was heated to 1,500 to 1,700° C. to generate vapor thereof. $N_2$ was fed at 1 to 5 liters/minute as carrier gas 2' and $N_2$ (for instance, 5 liters/minute) was fed as sheath gas 4' to synthesize $SnO_2$ gas sensor material particles having needle-shaped formes controlled by the evaporation-condensation reaction in reaction vessel 5'.

Next, the $SnO_2$ needle-shaped particles thus obtained were transferred to charting vessel 7'' and a negative electrostatic charge was applied thereto. Then sensor substrate 8 to which internal electrodes had been pre-attached was, for instance, grounded to deposit electrostatically needle-shaped particles on the substrate. As a result, a methane gas sensor was made on which needle-shaped particles were intertwined and were deposited in a porous state of high porosity under a power capable of forming rosary bead that was caused when the charged particles were deposited on the substrate.

$SnO_2$ particles for $SnO_2$—Pd composite particles were synthesized by MOCVD method.

Tetramethyl tin $Sn(CH_3)_4$ was brought to a gasification temperature of 0° C. with vapor generator 1 to generate $Sn(CH_3)_4$ vapor. The obtained $Sn(CH_3)_4$ vapor was transferred to reaction vessel 5, which was kept at a temperature of 500 to 800° C., using 0.01 to 0.5 liter/minute Ar as carrier gas 2. At the same time, 0.1 to 0.5 liter/minute $O_2$ as reaction gas 3 and 0 to 5 liters/minute $N_2$ as sheath gas 4 were fed to synthesize $SnO_2$ gas sensor material particles by a chemical reaction in reaction vessel 5.

Pd catalyst particles were synthesized by evaporation-condensation in a reducing gas.

Pd starting powder 6 was placed in reaction vessel 5' and reaction vessel 5' was heated to 1,500 to 1,700° C. to generate vapor thereof. Then 1 to 5 liters/minute $N_2$ were fed as carrier gas 2' and $N_2$ (for instance, 5 liters/minute) was fed as sheath gas 4' to synthesize Pd particles by an evaporation-condensation reaction in reaction vessel 5'.

Next, The $SnO_2$ gas sensor material particles thus obtained were transferred to charging vessel 7 and Pd catalyst particles were fed to charging vessel 7' and a positive electrostatic charge was applied to the $SnO_2$, while a negative electrostatic charge was applied to the Pd. The two were then mixed to synthesize $SnO_2$—Pd composite particles where Pd catalyst particles were deposited on the surface of $SnO_2$ gas sensor material particles by a power of the electrostatic cohesion which worked between the particles charged to opposite polarities.

Next, negative electrostatic charge was applied to the $SnO_2$—Pd composite particles. Then the sensor substrate for the methane sensor was grounded to deposte composite particles electrostatically on the substrate.

As shown in FIG. 2, a layer-built sensor was obtained where composite particles were deposited on the methane sensor in a porous state of high porosity by a power capable of forming rosary bead that was caused when the charged particles were deposited on the substrate.

(2) Results

Figure 3:
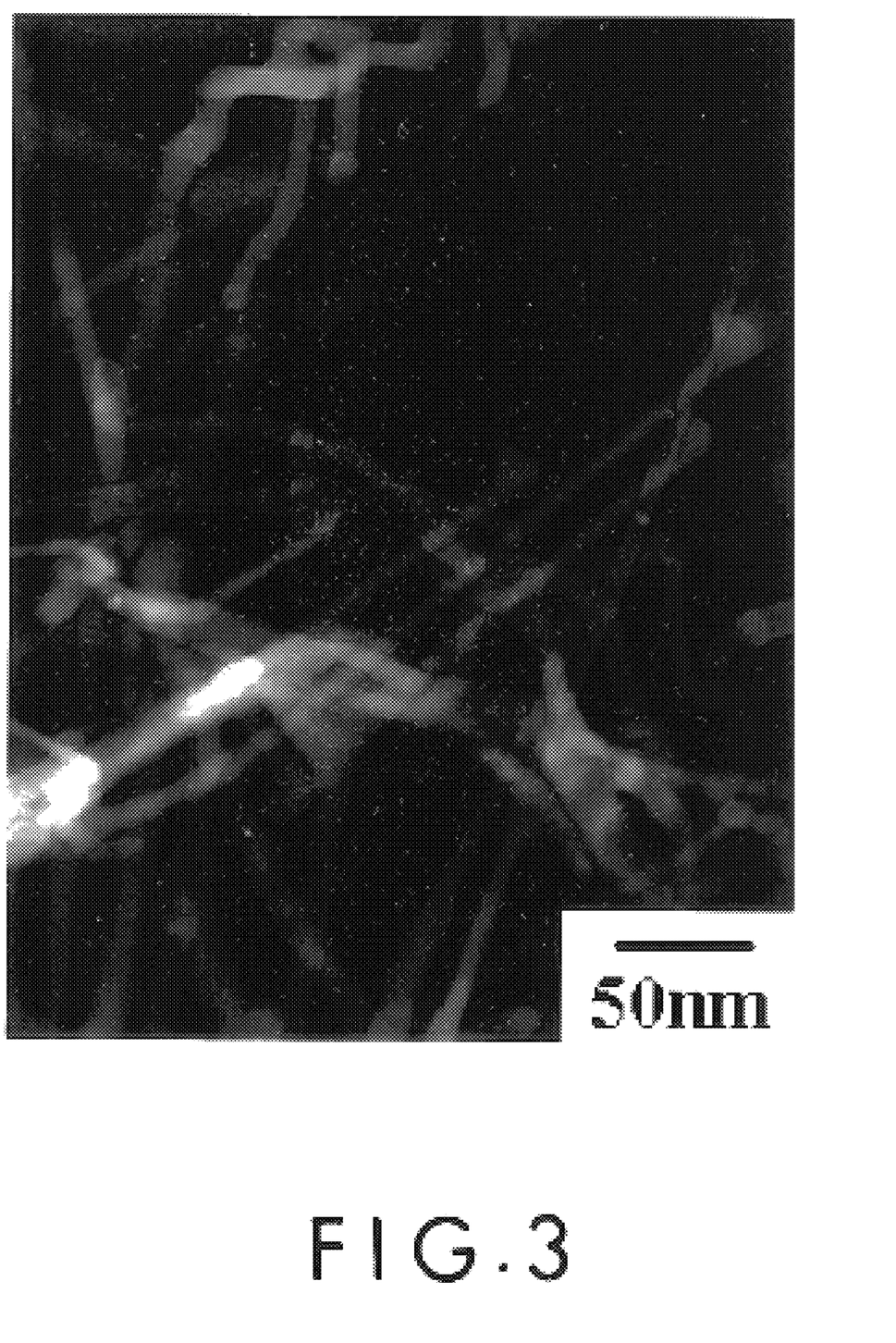
FIG. 3 is an electron micrograph of the $SnO_2$ needle-shaped particles synthesized by the present invention.

An electron micrograph of the $SnO_2$ needle-shaped particles obtained by the method of the present invention is shown in FIG. 3. These needle-shaped particles had an approximately uniform length of several 100 nm or longer.

Figure 4A:
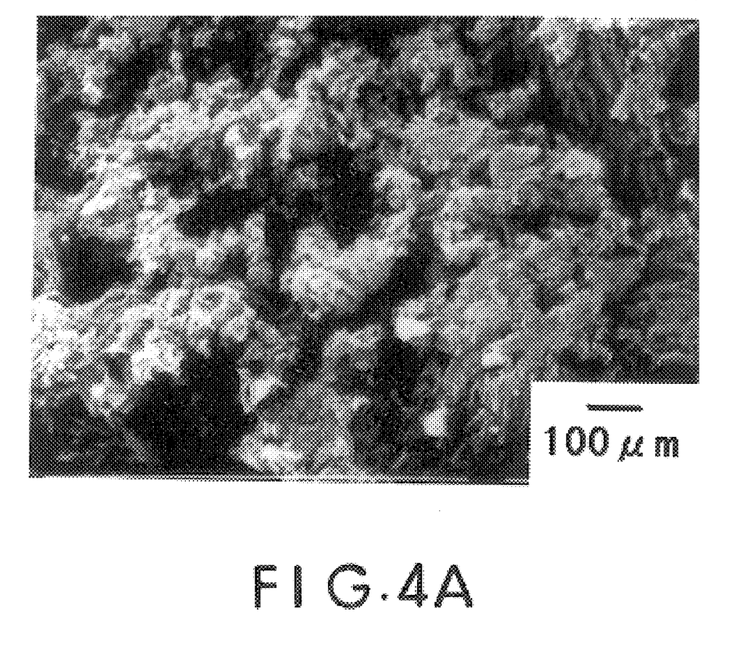
FIGS. 4A and 4B is an electron micrograph of the surface of a gas sensor element made from $SnO_2$ needle-shaped particles produced by the present invention.
Figure 4B:
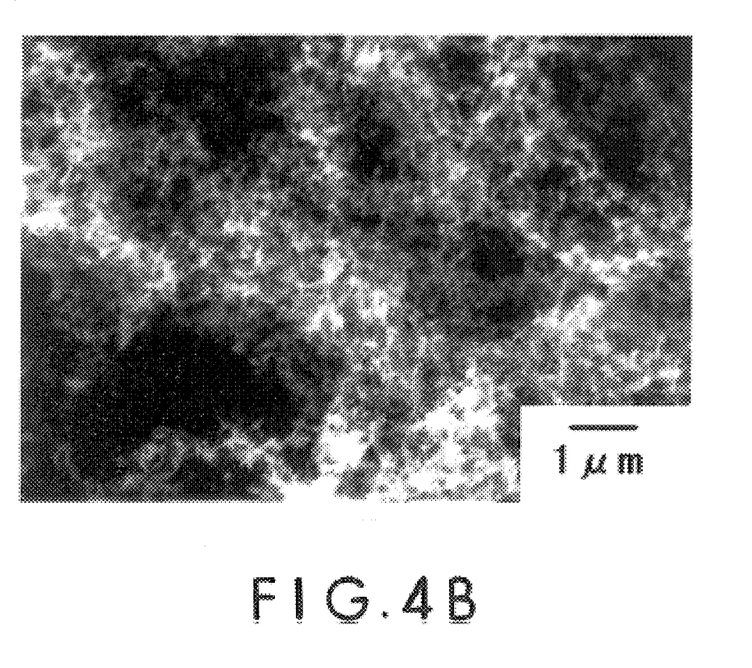

FIGS. 4A and 4B show an electron micrograph of the surface of a sensor made by the method of the present invention using the above-mentioned $SnO_2$ needle-shaped particles. This sensor has a porous thick film structure where needle-shaped particles are deposited in an intertwined state by the rosary bead forming function.

Figure 5:
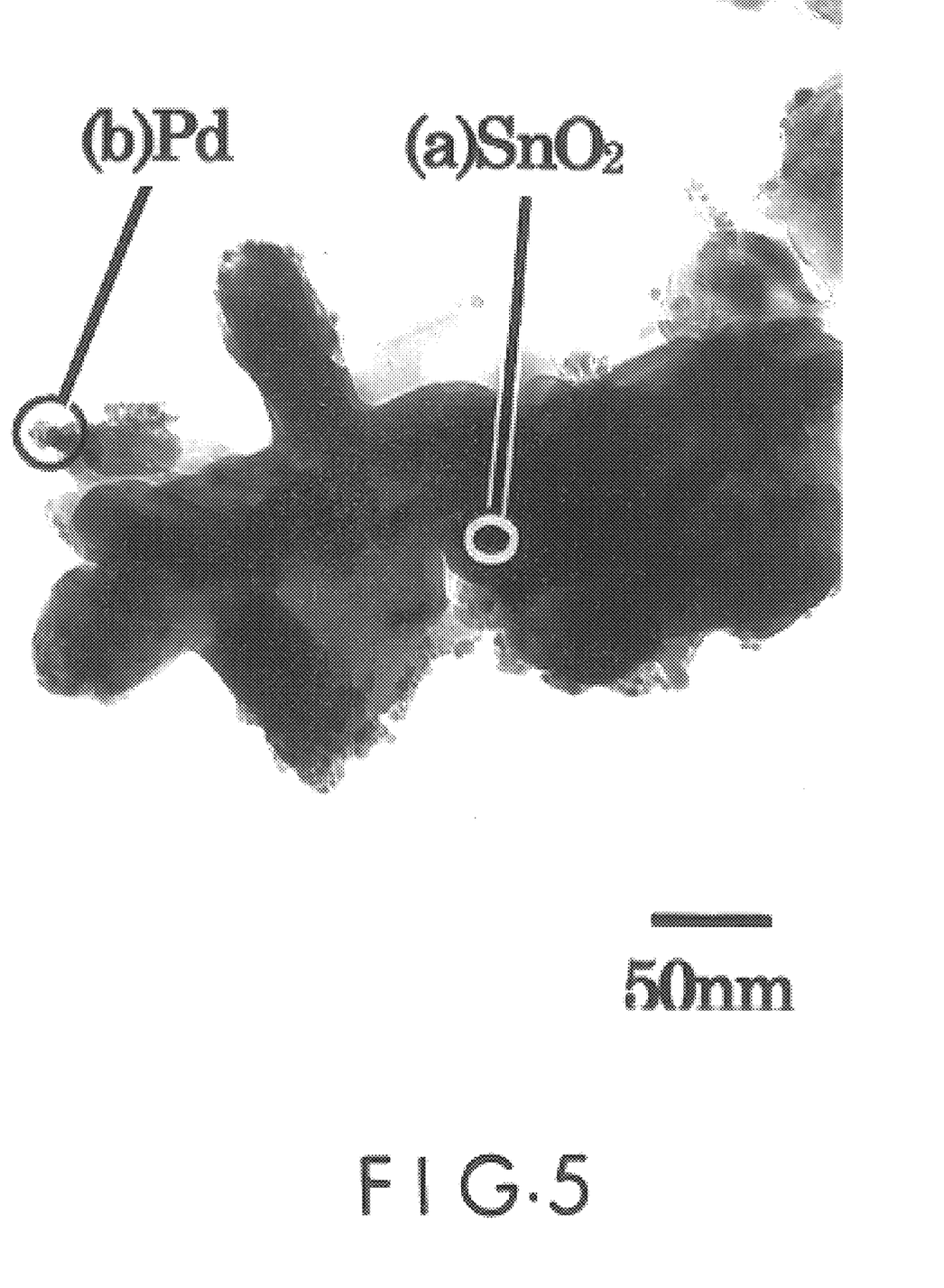
FIG. 5 is an electron micrograph of an example of the composite particles of $SnO_2$ gas sensor material particles and Pd catalyst particles obtained by the present invention.

FIG. 5 shows an electron micrograph of the $SnO_2$—Pd composite particles. These composite particles have a structure where Pd catalyst particles of 10 nm or smaller are uniformly deposited on the surface of $SnO_2$ gas sensor material particles that are 100 nm or smaller.

Figure 6A:
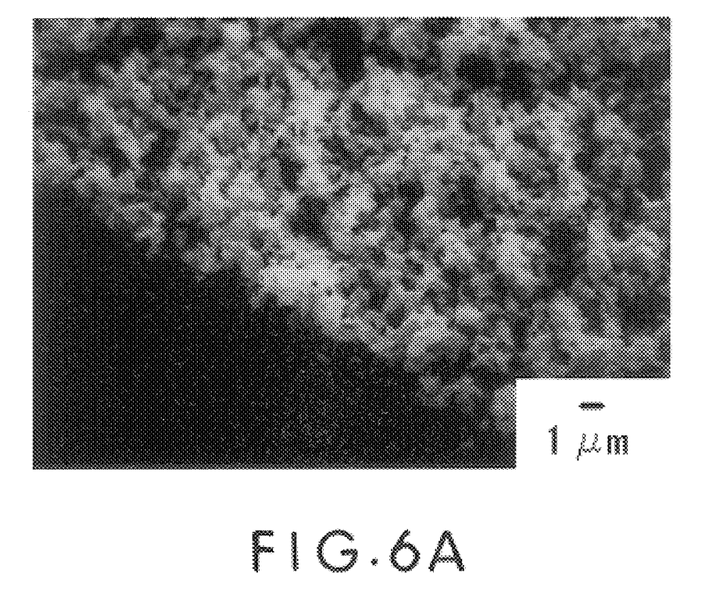
FIGS. 6A and 6B is an electron micrograph of the surface of a gas sensor element consisting of the $SnO_2$—Pd composite particles made by the present invention.
Figure 6B:
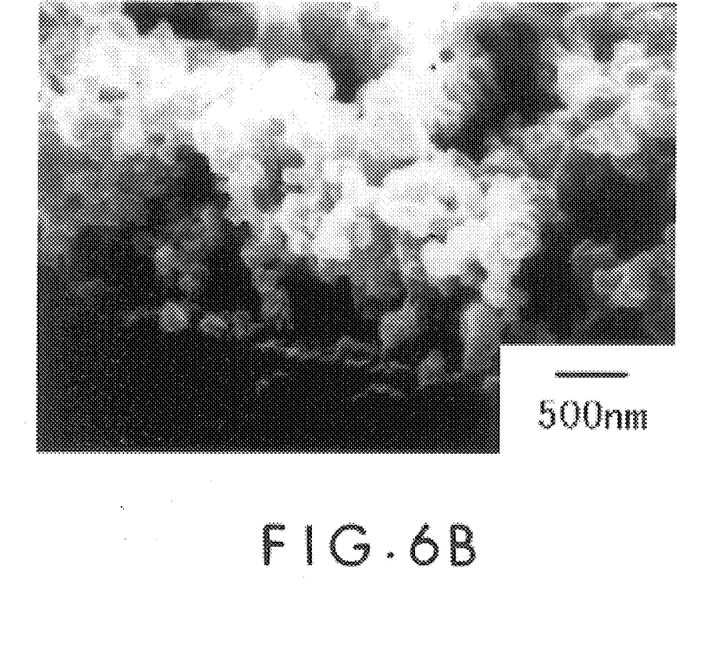

The electron micrograph of the surface of a sensor made by the method of the present invention using the above-mentioned $SnO_2$—Pd composite particles is shown in FIGS. 6A and 6B. A porous thick film structure where particles are deposited in a rosary bead state by the rosary bead forming function is obtained.

EXAMPLE 2

Figure 7A:
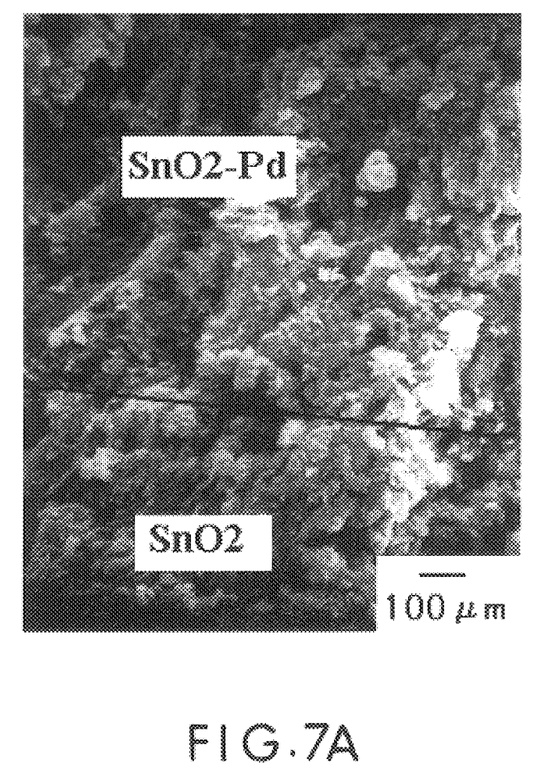
FIGS. 7A and 7B is an electron micrograph of the cross section of a layer-built sensor where the surface of a methane sensor consisting of $SnO_2$ needle-shaped particles is covered with a carbon monoxide sensor consisting of $SnO_2$—Pd composite particles made by the present invention.
Figure 7B:
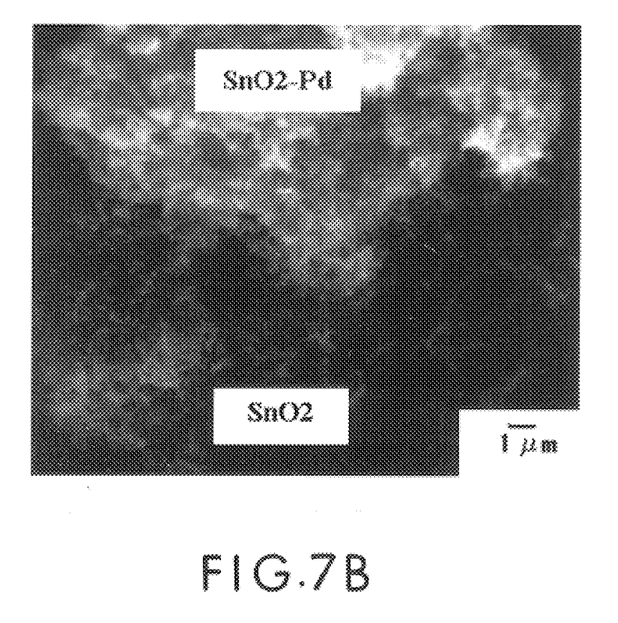

FIGS. 7A and 7B show an electron micrograph of the cross section of a layer-built sensor where the surface of the $SnO_2$ needle-shaped particle sensor in Example 1 is covered with $SnO_2$—Pd composite particle sensor. The layer below an arrow is the methane sensor layer and the layer above the arrow is the carbon monoxide sensor layer. A uniform coating was obtained over a broad area while maintaining the porous thick film structures of the two sensors.

EXAMPLE 3

Gas sensitivity of the layer-built sensor in Example 2 to methane and carbon monoxide is shown in Table 1. That is, Table 1 shows gas sensitivity of the layer-built sensor made by the present invention, that are an $SnO_2$ needle-shaped particle sensor and an $SnO_2$Pd composite particle sensor, to 0.4% methane and 0.04% carbon monoxide at a measuring temperature of 300° C. and 500° C. Gas sensitivity is represented as the ratio of resistance in air containing a specific amount of methane or carbon monoxide to sensor resistance in air. The concentration of the two gases was 0.4% methane and 0.04% carbon monoxide, which were the gas concentrations at which the alarms of hybrid gas leak sensors operate for city gas and incompletely burned gas, and measuring temperature was 300° C. on the low-temperature side and 500° C. on the high-temperature side. Moreover, a sensor made from $SnO_2$ needle-shaped particles only and a sensor made from $SnO_2$—Pd composite particles were used as sensors having no layer-built structure such that of the present invention to compare their gas sensitivities with those of the layer-built sensors. As a result, the $SnO_2$ needle-shaped particle sensor showed maximum sensitivity to both methane and carbon monoxide at the high temperature and showed no selectivity thereto. (However, this sensor using needle-shaped $SnO_2$ had relatively high sensitivity to methane, etc., even though containing no sensitizer.) On the other hand, although maximum sensitivity of the $SnO_2$—Pd composite particle sensor to carbon monoxide was shifted to the low-temperature side, their sensitivity to carbon monoxide was approximately ½ that to methane at a high temperature, which showed almost no selectivity thereto. However, the layer-built sensor, by using surface $SnO_2$—Pd composite particle sensor layer thereof on the low-temperature side and internal $SnO_2$ needle-shaped particle sensor layer on the high-temperature side, could selectively detect carbon monoxide at a low temperature and methane at a high temperature.

TABLE 1

| Type of sensor | Determination gas | Determination temperature and gas sensitivity | |
| --- | --- | --- | --- |
|  |  | 300° C. | 500° C. |
| $SnO_2$ needle-shaped | Methane | 2 | 8 |
| sensor | Carbon monoxide | 3 | 5 |
| $SnO_2$—Pd composite | Methane | 1.5 | 10 |
| particle sensor | Carbon monoxide | 9 | 4 |
| Layer-built | Methane | 1.4 | 11 |
| sensor | Carbon monoxide | 9 | 2 |

By means of the present invention, a layer-built structure where the surface of a methane sensor is covered with a carbon monoxide sensor can be made and a sensor capable of detecting several gases with good selectivity by 1 element can be provided, which is useful as a preferable gas sensor.

What is claimed is:

1. A semiconductor gas sensor element, comprising a layer-built structure of a methane sensor having at least one layer and a carbon monoxide sensor having at least one layer, wherein the surface of the methane sensor is covered with the carbon monoxide sensor, and the carbon monoxide sensor layer has an ability to act as a catalyst film capable of blocking the carbon monoxide, which impedes detection of methane gas, and having physical, electrical and chemical properties capable of detecting both methane and carbon monoxide with good selectivity the one said semiconductor gas sensor element.

2. The semiconductor gas sensor element according to claim 1, wherein said methane sensor is made from a needle-shaped semiconductor material particles as starting materials, and has a increased high reactivity to methane at a high temperature and simultaneously a low reactivity to methane at a low temperature.

3. The semiconductor gas sensor element according to claim 1, wherein said carbon monoxide is made from semiconductor-metal composite particles which are obtained by depositing metal particles with catalyst function on the surface of semiconductor gas sensor material particles synthesized by the gas phase method as the starting material, and has a increased high sensitivity to carbon monoxide on a low/temperature side of its temperature range dependance and decreased low sensitivity at a high temperature.

4. The semiconductor gas sensor element according to claim 1, wherein needle-shaped semiconductor particles and semiconductor-metal composite particles are used as the starting materials, and a porous thick film structure where these starting materials are deposited on a substrate in the form of rosary beads by electrostatic deposition.

5. The semiconductor gas sensor element according to claim 1, wherein the methane sensor is an $SnO_2$ based one and the carbon monoxide sensor is an $SnO_2$—Pd based one.

* * * * *